US007238866B2

(12) United States Patent  (10) Patent No.: US 7,238,866 B2
Zhang  (45) Date of Patent: *Jul. 3, 2007

(54) TRIPLOID HYBRID WATERMELON PLANTS

(75) Inventor: Xingping Zhang, Woodland, CA (US)

(73) Assignee: Syngenta Participations AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 10/795,609

(22) Filed: Mar. 8, 2004

(65) Prior Publication Data

US 2004/0172690 A1  Sep. 2, 2004

Related U.S. Application Data

(62) Division of application No. 10/145,980, filed on May 14, 2002, now Pat. No. 6,747,191.

(51) Int. Cl.
*A01H 5/00*  (2006.01)
*A01H 5/10*  (2006.01)
(52) U.S. Cl. .................................. 800/308; 800/298
(58) Field of Classification Search ............... 800/260, 800/269, 271, 308
See application file for complete search history.

(56) References Cited

U.S. PATENT DOCUMENTS

| 5,007,198 | A | 4/1991 | Gray et al. | |
| 5,523,520 | A * | 6/1996 | Hunsperger et al. | 800/260 |
| 6,018,101 | A | 1/2000 | Zhang | 800/274 |
| 6,747,191 | B2 | 6/2004 | Zhang | 800/308 |
| 2003/0172413 | A1 | 9/2003 | Barham et al. | 800/30 |
| 2003/0217395 | A1 | 11/2003 | Zhang | 800/308 |
| 2005/0034197 | A1 | 2/2005 | Zhang | 800/308 |
| 2006/0037110 | A1 | 2/2006 | Zhang | 800/308 |

FOREIGN PATENT DOCUMENTS

| RO | 115214 B | 12/1999 |
| RO | 115216 B | 12/1999 |
| WO | WO 00/70933 A | 11/2000 |
| WO | WO 03/051103 A | 6/2003 |

OTHER PUBLICATIONS

Henderson, W.R. J. Amer. Soc. Hort. Sci. 102(3): 293-297 (1977).*
Henderson et al. J. Heredity 89: 50-53 (1998).*
Eshed et al. Genetics 143: 1807-1817 (1996).*
Kraft et al. Theor Appl Genet 101: 323-326 (2000).*
Whealy, K. 1995. Garden Seed Inventory, Fourth Ed. pp. 596-610.*
Burpee Gardens 1986 pp. 2 and 156.*
Snyder et al (Mississippi State University Extension Service, Summer 2000).*
Gunter et al (Midwest Vegetable Variety Trial Report, Bulletin No. 2004-B17538, 2004).*
Synder et al (Regional Bulletin 06, Alabama Cooperative Extension System, Jul. 2001).*

Abbot & Cobb, Inc., *Vegetable Seeds for the Commercial Grower*, (Feasterville, PA) [catalog], 1992, pp. 70-73, 75.
*Asgrow, 1989 Vegetable Grower's Seed Guide*, (Kalamazoo, Michigan), pp. 61-62.
*Burpee Gardens*, W. Atlee Burpee Company (Warminster, PA) [catalog], 1986, pp. 156.
Compton et al., *Identifcation of tetraploid regenerants from cotyledons of diploid watermelon cultures in vitro* Euphytica, vol. 87, (1996) pp. 165-172.
El-Hafez et al., *Effect of Ploidy Differences on Fruit Characteristics in Watermelon* Acta Agronomica Academiae Scientiarum Hungararicae, No. 1/2, (1982) pp. 66-70.
*Garden Seed Inventory*, 4th Edition, Seed Saver Publications, (Decorah, Iowa, 1995), pp. 596-610.
*Gurney's Seed & Nursery*, 1998 Spring Catalog, (Yankton, SD), pp. 18.
*Hazera, Seed Catalog*, (Haifa, Israel), 1985, pp. 42.
Henderson, W.R. *Effect of Cultivar, Polyploidy and 'Reciprocal' Hybridization on Characters Imoprtant in Breeding Triploid Seedless Watermelon Hybrids* Journal of American Society for Horticultural Science, vol. 102, No. 3 (May 1977), pp. 293-297.
*Johnny's Selected Seeds*, (Albion, Maine) [catalog], 1997, pp. 69.
*Johnny's Selected Seeds*, (Albion, Maine) [catalog], 1999, pp. 70.
Karchi et al, *'Alena' Watermelon* HortScience, vol. 16(4) (1981) pp. 573.
Karchi et al, *The Importance of Cultural Practices in Materializing Yield Potential in a Tetraploid Watermelon Cultivar* Cucurbit Genetics Cooperative, No. 6 (1983) pp. 59-61.
*Known-You Seed*, (Kaohsiung, Taiwan), [catalog], 1991/1992, pp. 10, 12, 14, 15 21.
*Known-You Seed*, (Kaohsiung, Taiwan), [catalog], 1994, pp. 2, 9, 10, 12, 14, 17.
*Kyowa Seed, Descriptive Vegetable Seed Catalog*, A subsidiary of Mitsubishi Corporation (Tokyo, Japan), pp. 71, 73.
Levi A., "Biotechnology" in: Maynard, D.N. (ed.), *Watermelons: Characteristics, Production, and Marketing* (ASHA Horticulture Crop Production Series, 2001), pp. 74-77.
Li et al, *In vitro generation of tetraploid watermelon with two different dinitroanilines and colchicines* Cucurbit Genetics Cooperation Report, vol. 22, (1999) pp. 38-40.
Master's Touch brochure advertisement, Fresh Summit 2002 International Convention & Exposition, Oct. 11-15 in New Orleans, Louisiana.

(Continued)

*Primary Examiner*—David H. Kruse
*Assistant Examiner*—Keith O. Robinson
(74) *Attorney, Agent, or Firm*—Edouard G. Lebel; Bruce Vrana

(57) ABSTRACT

A tetraploid watermelon inbred 90-4194 is disclosed. The invention relates to the seeds and plants of tetraploid watermelon inbred 90-4194, the methods of propagating the tetraploid inbred 90-4194 through seeds and tissue culture. The invention also relates to methods of producing the triploid seedless watermelon seeds and plants by crossing inbred 90-4194 with diploid watermelon inbreds, and to the triploid plants produced therefrom. The invention further relates to the methods of developing new tetraploid lines by using tetraploid inbred 90-4194 as breeding material, and to tetraploid watermelon seeds and plants produced therefrom.

16 Claims, No Drawings

OTHER PUBLICATIONS

*Park Seed, Flowers and Vegetables*, (Greenwood, SC) [catalog], 1993, pp. 122.

*Rupp Seeds, Inc., Vegetable Seed Catalog*, (Wauseon, Ohio), 1999, pp. 46.

Schnitt, P., *A watermelon built for two: The seedless minis should be in stores this summer The Sacramento Bee*, [online], [retrieved on Jun. 20, 2002]. Retrieved from the Internet <URL: http://www.sacbee.com/content/business/v-print/story/2583893p-3116193c.html.

Seminis, Inc., index of company innovations [Online Index] *Personal Mini Seedless Watermelons*. Available: http://www.seminis.com/company/innovations/personal_watermelon.html (Mar. 4, 2003).

USDA, ARS, National Genetic Resources Program. *Germplasm Resources Information Network—(GRIN)*. [Online Database] National Germplasm Resources Laboratory, Beltsville, Maryland. Available: http://www.ars-grin.gov/cgi-bin/npgs/html/acchtml.PI1622527 (Mar. 6, 2003).

USDA, ARS, National Genetic Resources Program. *Germplasm Resources Information Network—(GRIN)*. [Onine Database] Plant Variety Protection Office, Beltsville, Maryland. Available: http://www.ars-grin.gov/cgi-bin/npgs/html/showpvp.PI200100260 (Mar. 6, 2003).

Ying et al, In vitro generation of tetraploid watermelon with two dinitroanilines and colchicines Cucurbit Genetics Cooperative, vol. 22 (1999) pp. 38-40.

Zang et al., "Generating Tetraploid Watermelon Using Colchicine in Vitro" in: Lester et al. (eds.), *Cucurbitaceae '94* (1995), pp. 134-139.

Zhang et al., *Shoot Regeneration from Immature Cotyledons of Watermelon Cucurbit Genetics Cooperative Report*, vol. 17 (1994), pp. 111-115.

Alexandru, D. D., [Database WPI], Section Ch, Week 200022, Derwent Publications, Ltd., London, GB; Class C06, AN 2000-254749, Dec. 30, 1999.

Alexandru, D. D., [Database WPI], Section Ch, Week 200022, Derwent Publications, Ltd., London, GB: Class C06, AN 2000-254747, Dec. 30, 1999.

Buttrose et al., Some effects of light intensity day length and temperature on growth of fruiting and nonfruiting watermelon citrullus-lanatus Annals of Botany, vol. 42, No. 179 (1978) pp. 599-608.

Crall et al., *Ssdl: A High-Quality Icebox Watermelon Breeding Line Resistant To Fusarium Wilt And Antracnose Hortscience*, vol. 29, No. 6 (Jun. 1994) pp. 707-708.

Fan et al. , Identification of Quantitative Trait Loci Associated with Fruit Traits in Watermelon (*Citrullus lanantus* (Thanb) Mansf) and Analysis of their Genetic Effects Acta Genetica Sinica, vol. 27, No. 10, (2000) pp. 902-910, abstract only.

Kano, Y., Effects of summer day-time temperature on sugar content in several portions of watermelon fruit (*Citrullus lanatus*) *Journal of Horticultural Science & Biotechnology*, vol. 79, No. 1 (Jan. 2004) pp. 142-145.

Karchi et al., Alena—a new tetraploid watermelon cultivar Hassadeh, vol. 61(8) (1981) pp. 1284-1285, 1320 [in Hebrew with English translation].

Maynard et al., Triploid Watermelon Production Practices and Varieties Acta Horticultural Science, NL, (1992) pp. 169-178.

Nerson et al, Pretreatments of seeds improve germination and emergence of polyploid watermelons *Hassadeh*, vol. 65(5) (1985), pp. 916-920 [in Hebrew with English translation].

Nerson et al, The effect of time of harvest on fruit ripening and keeping quality in two watermelon cultivars *Hassadeh*, vol. 62(4) (1982) pp. 606-607 [in Hebrew with abstract in English].

Pitchaimathu et al., Evaluation of triploid (seedless) watermelon under polyhouse South Indian Horticulture, South Indian Horticultural Association, Coimbatore, In, vol. 49, No. Special, (Aug. 2001), pp. 311-312.

Plant Variety Protection Certificate, United States of America Syngenta Seeds, Inc.—Owner, No. 200100260, Feb, 5, 2002; issued by Plant Variety Protection Office.

Sundstrom et al., *Influence Of Potassium And Calcium On Quality And Yield Of Watermelon Citrullus-Lanatus Cultivar Calhoun-Gray Journal of the American Society for Horticultural Science*, vol. 108, No. 5 (1983) pp. 879-881.

NeSmith, D. Scott et al, Fruit Set of Triploid Watermelons as a Function of Distance from a Diploid Pollinizer, *HortScience*, vol. 36 (1), Feb. 2001, pp. 60-61.

*Hazera Quality Seeds Ltd*., Seedless Fruit Hybrids, Standard Fruit Hybrid, and Open Pollinated (Israel) [catalog], 1999.

Molinar R. and Mueller S., Mini "Personal" Watermelon Variety Trial—2003, pp. 1-6 [online] [retrieved on Oct. 30, 2006]. Retrieved from the Internet: <URL http://cefreson.ucdavis.edu/Vegetable_Crops/.

Mueller S. and Molinar R., Mini "Personal" Watermelon Variety Trial—2004, pp. 1-9 [online] [retrieved on Oct. 30, 2006]. Retrieved from the Internet: <URL http://cefresno.ucdavis.edu/Vegetable_Crops/.

Affidavit of Dean G. Liere dated Nov. 27, 2006 (2 pages).

Affidavit of Dr. Xingping Zhang dated Feb. 23, 2007 (4 pages).

Jeffrey Adelberg and B.B. Rhodes, "Micropropagation from Zygotic Tissue of Watermelon," C.E. Thomas (ed.), Proc. of the Cucurbitaceae 89: *Evaluation and enhancement of cucurbit germplasm*, Charleston, S.C., USA.

P. Schnitt, "A watermelon built for two," Published 2:15 am PDT Friday, May 10, 2002 [online] [retrieved on May 16, 2002] Retrieved from the Internet: <URL: http://www.sacbee.com/content/business/story/2583893p-3116193c.html>.

* cited by examiner

US 7,238,866 B2

TRIPLOID HYBRID WATERMELON PLANTS

CROSS-REFERENCE TO RELATED APPLICATIONS

This application is a divisional of U.S. Application Ser. No. 10/145,980, filed May 14, 2002, now U.S. Pat. No. 6,747,191 the contents of which are incorporated herein by reference in their entirety.

FIELD OF THE INVENTION

This invention is in the field of watermelon breeding specifically relating to a tetraploid watermelon used to produce triploid seeds and plants for production of a substantially small sized seedless watermelon fruit.

BACKGROUND OF THE INVENTION

This invention relates to a new and unique inbred tetraploid watermelon line, designated 90-4194.

Watermelon is an important horticultural crop that accounts for 2% of the world area devoted to vegetable crops. There were 6,024,000 acres of watermelon grown in the world and 187,000 acres of watermelons grown in the United States in 1997. Asia is by far the most important watermelon production site with 72% of the world area and 77% of the world production (FAO Production Yearbook 51, 1998). The estimated annual world watermelon value exceeded $7.6 billion when using the United States average price for 1995-1997. The United States watermelon crop amounted to over 41 million cwt, from over 174,000 harvested acres, and a farm value of over $266 million, accounted for 9.2% of the harvested acres, 10.0% of the production, and 3.5% of the value of the United States fresh vegetable industry in 1999 (USDA Agricultural Statistics 2001). California was the leading state in watermelon farm gate value, exceeded $72 million in 2000, due to high percentage of triploid seedless watermelon grown in California. Seedless watermelon receives well above the average price for seeded watermelons in the market. Triploid seedless watermelon also produces higher yields than the diploid seeded watermelons.

Triploid seedless watermelon is a true F1 hybrid between a tetraploid watermelon, as the female parent, and a diploid watermelon, as the male parent (Kihara, H. 1951, *Triploid Watermelons,* Proceedings of American Society for Horticultural Science, 58:217-230). Regular watermelons, the seeded diploid watermelons, have 22 chromosomes (2N=2X=22) in their somatic cells. The tetraploid watermelons have 44 chromosomes (2N=4X=44) in their somatic cells. When female flowers of tetraploid plants are crossed pollinated by the male flowers of normal diploid plants, the seeds produced in the fruit of tetraploid plants are triploid seeds. Triploid seeds produce triploid plants. When the triploids plants are grown with the normal diploid plants in the same field, the triploid plants produce fruits that are seedless. The seedless condition in triploid watermelon is the result of the presence of three homologous sets of chromosome per somatic cell rather than the usual two. Cells with three sets of homologous chromosomes are said to be triploid and are designated as 3X. The triploid seedless watermelons have 33 chromosomes (2N=3X=33) in their somatic cells. The inability of the triploid zygote to produce normal viable gametes (pollen and egg cells) causes the absence of seeds in triploid fruits. Typically, seedless watermelons contain small edible white ovules, similar to those in immature cucumbers.

Triploid seedless watermelons have been commercially grown in the United States since the late 1980's. The popularity of seedless watermelon has increased since its commercial introduction in the United States. Most of the watermelons produced in California in 2001 were triploid seedless watermelons. Triploid varieties produce higher yields than the diploid seeded varieties, due to more fruit per plant and longer harvest period. The triploid seedless watermelon receives premium prices because of the high quality flesh virtually free of seeds.

SUMMARY OF THE INVENTION

The invention comprises a novel inbred tetraploid watermelon, designated 90-4194. The present invention includes the seeds of the inbred tetraploid watermelon line 90-4194, methods of producing hybrid triploid watermelon seeds using 90-4194, methods of producing seeds having all the genetics of 90-4194, and methods of developing new inbred tetraploid lines using 90-4194. This invention further includes triploid hybrid watermelon seeds and plants produced by crossing 90-4194 with a diploid watermelon line.

DETAILED DESCRIPTION OF THE INVENTION

In commercial production of triploid watermelon seed, tetraploid and diploid parental lines are planted in the same field. Cross-pollination between the tetraploid line, the female parental line, and the diploid line, the male parental line, are accomplished by either hand or bee pollination. Triploid watermelon seeds are produced only in melons of tetraploid plants that are fertilized with pollen of diploid plants. All commercially grown seeded watermelons are diploid; therefore, there are many diploid lines for use as diploid parents. The major limitation to development of seedless watermelon varieties lies in the availability of useful tetraploid parental lines.

Tetraploid watermelon lines are developed by doubling the chromosomes of regular diploid watermelon lines. Chromosome doubling was first accomplished with the toxic alkaloid colchicine by applying colchicine to the growing point of new emerged watermelon seedlings. Tissue culture methods have also been developed by Zhang, X. P., B. B. Rhodes, H. T. Skorupska, W. C. Bridges, 1995, *Generating Tetraploid Watermelon Using Colchicine in Vitro,* G. Lester & J. Dunlap et al. (eds.), Cucurbitaceae' 94: 134-139. Dinitroanilines have been used to double chromosome numbers, and their effectiveness has previously been compared with crops other than watermelon. Li et al (Li, Ying, J. F. Whitesides, B. Rhodes, 1999, *In vitro generation of tetraploid watermelon with two different dinitroanilines and colchicines,* Cucurbit Genetics Cooperative Rpt 22:38-40) compared in vitro chromosome doubling effectiveness using colchicine and the dinitroanilines, ethalfluralin (N-ethyl-N-2-methyl-2-propenyl)-2,6-dinitro-4-(trifluoromethyl) benzanine), and oryzalin (3,5-dinitro-N4, N4-dipropylsulfanilamide) and concluded that either ethalfluralin or oryzalin was preferable to colchicine.

Several treatment methods are used to induce tetraploids from diploids using the chemicals mentioned above. One method is to treat the seed before sowing. The seed are soaked in clean water for 5-6 hrs and then the seed are soaked in either colchicine solution (0.2%) or dinitroanilines (e.g. 35 $\mu M$ oryzalin) for 24 hrs. The seed are briefly rinsed before sowing. Dry seed can also be directly soaked in the chemical solution without pre-soaking in the water. This treatment is simple to do and is a good method to use if one has no restriction of seed supply. The treatment usually reduces the germination and emergence. The second method is to treat the new emerged seedling. The diploid inbreds are sown in greenhouse in seedling flats. The soil temperature is kept at 29-31° C. for rapid and uniform germination. One drop of colchicine (0.1%) or dinitroanilines (e.g. 35 µM oryzalin) solution is added to the shoot apex between the cotyledons as soon as the seedling has emerged from soil. The colchicine solution is applied to the growing point in the morning or evening for three consecutive days. We get good chromosome doubling from one application of oryzalin. Another method is to treat the shoot apex of germinated seed after which the germinated seed is planted into soil. The seeds are germinated in an incubator at 30° C. When the radicals are about 2 cm long, the portion above the hypcotyls of germinated seeds is immersed upside down into colchicine (0.1%) or dinitroaniline solution (35 UM oryzalin) for 10-15 hrs at 30° C. in an incubator. The treatment should be conducted in a high humidity chamber or box to assure that the radicals/roots are not desiccated. The seeds are then washed and planted in the soil. The last two methods, although more tedious to use, usually give better recovery of tetraploid events as the root system is not affected by the treatment.

The next step is to develop tetraploid lines from individual converting events. The selected tetraploid individuals based on morphological expression are self-pollinated and the resulting seeds are planted in the next generation as lines. These lines are again self-pollinated and compared for fertility and horticultural traits. Only the desirable lines are selected if there is difference among these lines. Desirable lines may be bulk harvested if there is no variation within the line and among selected lines. Further seed increases may be conducted in an isolation block. Mass selection may be conducted for this increase in the isolation plot and thereafter. Fertility of the tetraploid may be improved in subsequent generations.

The use of tissue culture to propagate tetraploid watermelon plants is further exemplified in Adelberg, J. W., B. B. Rhodes, *Microprogpogation from zygotic tissue of watermelon,* C. E. Thomas (ed.) Proc. of the Cucurbitaceae 89: *Evaluation and enhancement of cucurbit germplasm,* Charleston S.C., USA; and Zhang et al., *Shoot regeneration from immature cotyledon of watermelon,* Cucurbit Genetics Coop. 17:111-115 (1994).

Crossing two different tetraploids and then going through recombination breeding can also result in new tetraploid lines. A longer breeding period is required to develop a stable tetraploid line using this approach. This is due to the larger number of combinations and the fewer seed that tetraploids produce. However, some breeders make good progress by taking this approach.

Because meiosis is sometimes irregular in autotetraploids, diploids and aneuploids do occur in their offspring. The leaves, flowers and pollen grains of tetraploids are morphologically distinct from diploids (Zhang, X. P., B. B. Rhodes, H. T. Skorupska, W. C. Bridges, 1995, *Generating Tetraploid Watermelon Using Colchicine in Vitro,* G. Lester & J. Dunlap et al. (eds.), Cucurbitaceae' 94: 134-139). Tetraploids also have a different number of chloroplasts in the guard cells (Compton, M. E., D. J. Gray and G. W. Elmstrom. 1996, *Identification of tetraploid regenerants from cotyledons of diploid watermelon cultures in vitro,* Euphytica 87:165-172). These morphological traits can help breeder to eliminate the diploids and aneuploids occurring in the tetraploid population during sexual propagation.

Triploid seeds are currently produced using two methods, the bee-pollination method and the hand-pollination method. In the United States, the bee-pollination method is used to produce triploid watermelon seed. Almost all of the United States triploid watermelon seed production is located in Northern California. The production fields are typically planted in a ratio of 2 rows of tetraploid female line and 1 row of diploid male line. All the male flower buds are manually removed from the female tetraploid plants. This process is known as de-budding. The female flowers are open-pollinated by bees. The fruit set during the de-budding period are marked and harvested for triploid hybrid seed. Male buds are manually removed from tetraploid female vines throughout the pollination season. If a male sterile tetraploid line is available, workers can easily remove the male fertile plants in the tetraploid female row with much less time and efforts. All the fruit set on the male-sterile tetraploid plants can be harvested for hybrid triploid seed. When the marked male-sterile system is used, seed producer can insure that no female off-types exist in the female tetraploid line and the hybrid triploid seed (Zhang, X. P. and B. B. Rhodes, 2000, Method using male sterility and a marker to produce hybrid seeds and plants; U.S. Pat. No. 6,018,101).

Hand-pollination is mainly used to produce triploid watermelon seed in areas where isolation is not available and several triploid hybrids are produce in the same field block. Inbred male parent line is sown 7-10 days earlier than inbred female tetraploid parent line. The male parent is usually located outside of the crossing block. Approximately four to ten tetraploid female plants per male plant are planted to insure adequate pollination. The male parent is carefully checked for its uniformity before male flowers are collected. Any off-types that can be recognized based on plant morphology and ovary characteristics are removed. Pollination starts when the second female flowers of the tetraploid female parent are ready to flower. The female flower buds of the tetraploid female parent line are identified and covered with paper cups or small paper bags before they bloom the next morning. Male flowers of the diploid male parent line are collected in the early morning before the visit of bees or other pollination insects to the flowers. The covered female flower buds are then uncovered and pollinated using the collected fresh male flowers. The pollinated female flowers are then re-covered and marked. The open-pollinated fruits on the female parent plants are removed periodically to insure the development of hand-pollinated fruits. Male plants are removed from the field after pollination is complete to insure that only fruit from female parents are harvested.

Inbred 90-4194 was developed in northern California by converting diploid inbred HD to a tetraploid watermelon. The conversion from diploid (2X) to tetraploid (4X) was accomplished using an oryzalin protocol comprising the following steps:

In November of 1999, seeds of HD were seeded in a 50-cell plastic seedling tray in the greenhouse. One drop of 35 µM oryzalin was added to the meristem tip between 2 cotyledons each of the newly emerged seedlings. Treatment of all the seedlings with oryzalin was finished about 10 days after sowing.

Seedlings were watered and fertilized periodically.

In late December of 1999, putative tetraploids were transplanted into 2-gallon pots filled with Pro-Mix BX soil-less soil in the greenhouse. During the course of plant development, diploid (not converted) plants and branches were removed based on leaf morphology and male flower characteristics.

Following is the chronological order of development of tetraploid line 90-4194:

Generation Season/Year Description $T_0$ Spring 2000 At the seedling transplant stage, 72 putative tetraploids were transplanted into 2-gallon pots in greenhouse. Non-converted plants and branches were identified based on leaf morphology and male flower characteristics, and were removed. Only the female flowers from true tetraploid plant/branches were self-pollinated. At full fruit maturity, fruit with large blossom end scars (2-3 times that of its diploid version) were harvested and examined for fertility as suggested by number of seed per fruit. Four individual selections 4XHD-1, -2, -3, and -4 and one bulk selection 4XHD-B were made to plant the $T_1$ generation.

$T_1$ Summer 2000 4XHD-1 and 4XHD-2 were planted in the greenhouse for further selection and seed increase. 4XHD-3 and 4XHD-4 were planted in the field for field observation and seed increase. 4XHD-B was planted in the crossing block in the field to make triploid hybrids. 4XHD-2 was not as good as 4XHD-1 at the seedling stage and was discarded. 42 plants of 4XHD-1 were grown to maturity in the greenhouse. All the seeds of 4XHD-1 were bulk-harvested and labeled as 4XHD-1-B as no variation was observed in this line. No variation was observed within and between 4XHD-3 and 4XHD-4. Therefore seeds were also bulk-harvested and labeled as 4XHD-3/4.

Fall 2000 Five triploid hybrids derived from 4XHD-B were evaluated in Florida. Three hybrids were unique and promising triploid hybrids.

$T_2$ Spring 2001 About 700 plants of 4XHD-1-B were planted in a plastic greenhouse for generation advance and seed increase. Hand pollination was conducted. No variation was observed. All the fruits are uniform and true to type. Seeds were bulk-harvested and named as 90-4194.

$T_3$ Summer 2001 About 3500 plants of 90-494 were transplanted to a one-acre isolation plot for stock seed increase using bee-pollination. 1200 plants of 90-4194 were transplanted into 2 net covered cages for foundation seed increase by hand pollination. No variation was observed from cage and field plantings. The breeding process is finished and seeds harvested serve as foundation and stock seed.

The unique characteristics of inbred 90-4194 are described as follows:

90-4194 is a very early maturing tetraploid watermelon. Fruit matured 24-27 days after flowering under summer conditions in Northern California. Other commercial tetraploids take at least 35 days under the same conditions.

The fruit of 90-4194 is very small, about 2 kg, only ¼-⅓ the size of the tetraploids commercially used. The fruit shape is round and skin color is light green with green pencil lines. The flesh is firm and red with refractometer % soluble solids of 13%.

The seeds of 90-4194 are small, about 31 g per 1000 seeds, ½-⅓ the weight of commercially used tetraploids. 90-4194 produces about 80 seeds per fruit. The seed color is medium brown.

The rind of 90-4194 is very thin, 4-7 mm, ½-⅓ the thickness of commercially used tetraploids. This thin rind splits easily under dry conditions with great relative humidity fluctuations.

90-4194 has excellent fruit setting ability under poor environmental conditions. When this tetraploid was grown in the plastic greenhouses without supplement lights in the early spring of 2001 at Syngenta's Woodland research station with other 23 diploid and 1 tetraploid breeding lines, 90-4194 was the only watermelon line setting fruits normally. Most of the watermelon lines did not produce any fruit due to poor growing conditions.

90-4194 can produce multiple fruits per plant. One plant of 90-4194 can bear as many as 4 fruits per plant. 90-4194 can also produce fruit in a long period of time. 90-4194 produced 2 crops from one planting during stock seed increase in the summer of 2001 Northern California. After harvest of first fruit set 90-4194 produced a second fruit set with excellent seed yield.

90-4194 produces triploid hybrids with fruit size about 3 kg or smaller. All the traditional triploid hybrids have much bigger fruits, most are above 6 kg.

Tetraploid watermelon inbred 90-4194 can be multiplied through vegetative propagation and sexual propagation. The vegetative propagation can be done preferably via shoot proliferation and then rooting in tissue culture. The detailed methods were described by Zhang et al. (Zhang. X. P., B. B. Rhodes, H. T. Skorupska, W. C. Bridges. 1995. Generating Tetraploid Watermelon Using Colchicine in Vitro. G. Lester & J. Dunlap et al. (eds.), Cucurbitaceae' 94: 134-139). This method is briefly described as follows: A) Collect shoot-tips and axiliary buds from greenhouse, field or laboratory grown plants of 90-4194. Rinse the shoot-tips and axillary buds under tape water for 30 minutes to an hour. Sterilize the shoot tips and axillary buds in 10% of household bleach for 8-10 minutes. Rinse the shoot-tips and axillary buds three times in sterilized distilled water. B) Culture the shoot-tips and axillary buds on Murashige and Skoog (MS) medium with 10 μM BA for shoot proliferation. Make a subculture every 3-4 weeks. C) Root the proliferated shoot buds on MS medium with 5-10 μM IBA for about 2 weeks. D) Acclimatize the rooted plantlets in a temperature and humidity controlled greenhouse. E) Grow the micropropagated plants in an isolation plot and harvest the seed from these plants.

Tetraploid watermelons are usually sexually propagated through seed. We have successfully propagated inbred 90-4194 in the greenhouse, in a net covered cage, and in the open fields. The seed increase field should be isolated from any other watermelon by at least 1.5 KM, if the seed increase is conducted in the open field. Good pest management and cultural practices should be implemented. Higher (20-30% higher than those used for commercial hybrid fruit production) levels of phosphate and potassium fertilize are beneficial for producing high seed yield and good seed quality. Calcium is supplemented for the fields low in calcium to minimize the fruit loss due to fruit splitting. Beehives are placed in the seed production fields to insure good pollination, the key biological event for seed production. Fruit is preferably harvested before fruit split and deterioration. The harvested fruit is then stored under room temperature for a period of time before extracting seed from fruit, to allow further embryo development and seed maturation in the fruit. The seed, after being extracted from the flesh, is thoroughly washed and quickly dried using a forced-air dryer to best maintain the seed viability.

The primary use of tetraploid watermelon is to make triploid hybrid watermelon seeds and plants that produce seedless fruit. The tetraploid line is used as female parent to cross with the diploid watermelon lines, the male parent lines. The creation of a desirable triploid hybrid heavily relies on the performance, especially seed producibility, and the combining ability of the tetraploid parent. Tetraploid watermelon inbred 90-4194 of the invention is a novel tetraploid line for creating triploid seedless watermelon hybrids having excellent fruit quality, small fruit size (personal size in the range of 2-3 KG), early maturity and excellent fruit setting ability. Most tetraploids are very difficult or fail to produce triploid seed when they are grown in greenhouse. However, inbred 90-4194 produced triploid seed with good seed yield in the greenhouse. Inbred 90-4194 also produced triploid seed in the field. Inbred tetraploid watermelon 90-4194 has very good combining ability in creating triploid hybrids. With limited exploration, 3 desirable triploid hybrids were created by crossing inbred 90-4194 with different diploid male lines.

Several methods can be used to produce triploid seeds from inbred 90-4194, once the proper combination is determined. Two commonly used methods are described here. Variations to these methods can be made according to actual production situation.

Hand-pollination method. This is the most often used method for producing triploid seed from 90-4194. The inbred tetraploid female parent 90-4194 and the inbred diploid male parent line are planted in the same field. The inbred male parent is planted 7-10 day earlier than the female parent 90-4194 to insure adequate pollen supply at the pollination time. The male parent and female parent 90-4194 are planted in the ratio of 1 male parent to 4-10 female parents. The diploid male parent may be planted at the top of the field for efficient male flower collection during pollination. Pollination is started when the second female flower on the tetraploid female parent 90-4194 is ready to flower. Female flower buds that are ready to open the next day are identified, covered with paper cups or small paper bags that prevent bee or any other insect visit of the female flowers, and marked with any kind of material that can be easily seen the next morning. This process is best done in the afternoon. The male flowers of the diploid male parent are collected in the early morning before they are open and visited by pollinating insects. The covered female flowers of the tetraploid female parent, which have opened, are uncovered and pollinated with the collected fresh male flowers of the diploid male parent, starting as soon as the male flower sheds pollen. The pollinated female flowers are again covered after pollination to prevent bees and any other insects visit. The pollinated female flowers are also marked. Only the marked fruits are harvested for extracting triploid hybrid seed.

Bee-pollination method. Using the bee-pollination method, the tetraploid female parent 90-4194 and the diploid male parent are usually planted in a ratio of 2 rows tetraploid parent to 1 row male parent. The female tetraploid plants are pruned to 2-3 branches. All the male flower buds on the female tetraploid parent plants are removed manually, (the de-budding process), during the pollination season on a daily basis. Beehives are placed in the field for transfer of pollen by bees from the male parent to the female flowers of the female parent. Fruits set during this de-budding time are marked. Only the marked fruits are harvested for extracting hybrid triploid seed.

The fruit of inbred 90-4194 split easily when they reach maturity, due to its extremely thin rind. This can be a serious problem when the seed production is conducted under conditions of dramatic humidity fluctuations. Thus, the fruit is harvested right before the splitting, and stored in shade for a period of 2-3 weeks. The rind becomes durable when the fruit is removed from the vine, and the embryos continue to develop in the harvested fruit, resulting in better seed quality.

According to the invention, tetraploid inbreds are used as parental lines to develop new tetraploid lines. The unique desirable traits of 90-4194 make it also very useful as a parental line in the development of new tetraploid inbreds. 90-4194 can be used as either female or male parent to cross with another inbred or hybrid tetraploid to develop new tetraploid inbreds.

| Description of the tetraploid inbred 90-4194 | |
|---|---|
| Fruit: | round, small |
| Area of best adaptation: | most areas |
| Emergence of anthesis: | 5 days earlier than the commercial tetraploid variety 90-4231 |
| Pollination to maturity: | 7 days earlier than the commercial tetraploid variety 90-4231 |
| Ploidy: | tetraploid |
| Cotyledon: | flat |
| Sex: | monoecious |
| Number of Main Stems: | 3 at crown |
| Number of flowers at first fruit set: | 18 staminate |
|  | 4 pistillate |
| Stem: | round, pubescent, 7 mm diameter at second node |
| Internode length | 7 cm |
| Flower at first fruit set: | staminate 3 cm across |
|  | pistillate 3 cm across |
|  | color yellow |
| Mature fruit size: | round, 15 cm long, 15 cm diameter at midsection, 2 kg average weight, smooth, light green rind with pencil lines, mottle/net |
| Rind: | brittle, 4 mm thick blossom end, 7 mm thick sides |
| Flesh: | crisp, fine with little fiber, medium red, 13% soluble solids of juice, no hollow heart, placental separation, or transverse crack |
| Seed: | 7 mm long, 5 mm wide, 2 mm thick, index (length ÷ width × 10) is 14, 31 gm per 1000 seed, 80 seed per fruit, dark brown |
| Sunburn: | resistant |

In contrast, the commercial tetraploid line 90-4231 has a fruit size of approximately 6-7 kg, and expresses some hollow heart, placental separation, and transverse crack.

In summary, the uniqueness of the inbred tetraploid watermelon line 90-4194 of the invention includes the following: a) The tetraploid 90-4194 produces a fruit that is significantly smaller than the fruit of conventional tetraploids, approximately ⅓ the size of conventional tetraploids; b) The tetraploid 90-4194 displays exceptional fruit set ability. In Honduras, the tetraploid 90-4194 is able to produce 3 crops (harvest of triploid seed from the tetraploid plant) from 1 planting, whereas conventional tetraploid plants allow for only 1 such harvest. Likewise, in California, Peru, and Chile, the 90-4194 of the invention produces 2 crops from 1 planting. c) The tetraploid 90-4194 produces 34 fruits per plant in a greenhouse setting, whereas conventional tetraploids typically produce on the average of less than 1 fruit per plant. d) The tetraploid 90-4194 matures 7 to 10 days earlier than regular tetraploids as measured from flower to fruit maturity. e) The tetraploid seed of 90-4194 of the invention is much smaller in size than the seed of conventional tetraploids. Twelve to 17 seeds of conventional tetraploid watermelon make a gram. In contrast, 35 to 39 90-4194 seeds of current invention make a gram. f) The fruit rind of 90-4194 is about ½ to ⅓ of the regular tetraploids. g) The seed yield of the 90-4194 tetraploid plant is significantly better than most of the tetraploids created with the same technique. 90-4194 produces as many as 150 triploid seed per fruit when pollinated by diploid male parent. Most of the recently developed tetraploid watermelons typically produce about 10 to 75 triploid seed per fruit when pollinated by diploid male parents.

The triploids watermelon fruit grown from triploid seed produced by the tetraploid plant of the invention display commercially important and novel traits. The uniqueness of the triploids produced by 90-4194 according to the invention, compared to conventional seedless watermelon, includes a) small fruit size, b) more fruit per plant, c) higher sugar content (the SSC), (see the chart below), d) thin rind, usually ½ or ⅓ the thickness of conventional triploids, e) the triploid fruit mature about 7-10 days earlier than regular triploid seedless watermelon fruit, f) the triploids developed from the tetraploid 90-4194 of the invention are more tolerant to hollow heart, a common defect of triploid seedless watermelon. Hollow heart on triploid seedless watermelon RWT 8123 and RWT 8124 has not been observed. RWT 8123 and RWT 8124 are triploids produced by the tetraploid 90-4194. and g) excellent fruit set ability.

The following chart shows the average weight (Avg. Wt.), the number of fruit per plant (Frt/plant) and the amount of soluble solids (mostly sugar) in the fruit flesh (SSC %). Tri-X-313 is a standard sized commercial triploid seedless watermelon, using a conventional tetraploid watermelon as the female parent. RWT8123 and RWTS124 are triploid seedless watermelons using the tetraploid 90-4194 watermelon of the invention as the female parent. The male diploid parents of the Tri-X-313, RWT8123, and RWT8124 lines were chosen for their significantly different phenotypes.

| Tri-X-313 | | | | RWT8123 | | | | RWT8124 | | | |
|---|---|---|---|---|---|---|---|---|---|---|---|
| Spacing | Avg. Wt. (lbs) | Frt/ plant | SSC % | Spacing | Avg. Wt. (lbs) | Frt/ plant | SSC % | Spacing | Avg. Wt. (lbs) | Frt/ plant | SSC % |
| 80" × 36" | 12.2 | 1.7 | 11.7 | 80" × 12" | 4.1 | 2.2 | 13.3 | 80" × 18" | 5.4 | 3.1 | 13.7 |
| 80" × 36" | 12.1 | 1.8 | | 80" × 24" | 4.5 | 3.5 | | | | | |
| 80" × 36" | 12.5 | 1.6 | | 80" × 36" | 4.5 | 4.5 | | | | | |

In accordance with the method of the invention, it is preferable to select the diploid male parents on the basis of small fruit size, ideally less than 8 lbs. In addition, the skin color and stripe pattern that is desired for the triploid watermelon is selected from the diploid male parent, as the skin color and stripe pattern (non) of 90-4194 are recessive to all other skin color and stripe patterns. Diploid male parents are also selected for their small seed size to reduce the size of the white seed ovules in the triploid fruit.

Although the foregoing invention has been described in some detail in this document, it will be obvious that changes and modification may be practiced within the scope of he invention, as limited only by the scope of the appended claims.

DEPOSIT

Applicants have made a deposit of at least 2500 seeds of watermelon inbred line 90-4194, and watermelon triploid hybrids RWT 8123. RWT 8124 and Tri-X-313 with the American Type Culture Collection (ATCC), Manassas, Va., 20110-2209 U.S.A., ATCC Deposit No: PTA-4855, PTA-6240, PTA-6241 and PTA-7049, respectively. This deposit of the watermelon inbred line 90-4194, and watermelon triploid hybrids RWT 8123, RWT 8124 and Tri-X-313 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. A triploid hybrid watermelon seed, wherein said triploid hybrid watermelon seed is produced by crossing a plant of tetraploid watermelon line 90-4194, representative seed of said tetraploid watermelon line having been deposited under ATCC Accession No. PTA-4855, with a diploid watermelon plant, wherein a plant of said triploid hybrid watermelon seed produces a fruit with an average weight of 3 kg or less, wherein the rind of said fruit has ½ to ⅓ the thickness of the rind of a fruit of a plant of watermelon triploid hybrid Tri-X-313, representative seed of said watermelon triploid hybrid having been deposited under ATCC Accession No. PTA-7049.

2. The triploid hybrid watermelon seed according to claim 1, wherein a plant of said triploid hybrid watermelon seed produces a fruit with an average weight of about 2 kg to 3 kg.

3. The triploid hybrid watermelon seed according to claim 1, wherein a fruit of a plant of said triploid hybrid watermelon seed matures about 7 days to about 10 days earlier than a fruit of a plant of Tri-X-313.

4. A triploid hybrid watermelon plant grown from the seed according to claim 1.

5. A triploid hybrid watermelon plant grown from the seed according to claim 2.

6. A triploid hybrid watermelon plant grown from the seed according to claim 3.

7. Fruit of a triploid hybrid watermelon plant according to claim 4.

8. Fruit of a triploid hybrid watermelon plant according to claim 5.

9. Fruit of a triploid hybrid watermelon plant according to claim 6.

10. A method for producing triploid watermelon fruit comprising:

a) growing in a field a triploid hybrid watermelon plant according to claim 4;

b) allowing said plant to set triploid watermelon fruit; and c) harvesting said triploid watermelon fruit.

11. A method for producing triploid watermelon fruit comprising:

a) growing in a field a triploid hybrid watermelon plant according to claim 5;

b) allowing said plant to set triploid watermelon fruit; and c) harvesting said triploid watermelon fruit.

12. A method for producing triploid watermelon fruit comprising:

a) growing in a field a triploid hybrid watermelon plant according to claim 6;

b) allowing said plant to set triploid watermelon fruit; and c) harvesting said triploid watermelon fruit.

13. The triploid hybrid watermelon seed according to claim 1, wherein said diploid watermelon plant produces a fruit of less than about 8 lbs.

14. A triploid hybrid watermelon plant grown from the seed according to claim 13.

15. Fruit of a triploid hybrid watermelon plant according to claim 14.

16. A method for producing triploid watermelon fruit comprising:

a) growing in a field a triploid hybrid watermelon plant according to claim 14;

b) allowing said plant to set triploid watermelon fruit; and c) harvesting said triploid watermelon fruit.

* * * * *